(12) United States Patent
Anand (10) Patent No.: US 10,987,084 B2
(45) Date of Patent: Apr. 27, 2021

(54) ULTRASOUND SYSTEM AND METHOD

(71) Applicant: Carestream Health, Inc., Rochester, NY (US)

(72) Inventor: Ajay Anand, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 1077 days.

(21) Appl. No.: 15/461,516

(22) Filed: Mar. 17, 2017

(65) Prior Publication Data

US 2017/0372019 A1 Dec. 28, 2017

Related U.S. Application Data

(60) Provisional application No. 62/355,369, filed on Jun. 28, 2016.

(51) Int. Cl.

| | |
|---|---|
| *A61B 8/00* | (2006.01) |
| *G06Q 50/22* | (2018.01) |
| *G16H 40/40* | (2018.01) |
| *G16H 40/63* | (2018.01) |
| *G16H 40/20* | (2018.01) |
| *G16H 30/20* | (2018.01) |
| *G06Q 10/10* | (2012.01) |

(52) U.S. Cl.
CPC ............. *A61B 8/4405* (2013.01); *A61B 8/00* (2013.01); *A61B 8/4427* (2013.01); *A61B 8/4438* (2013.01); *A61B 8/461* (2013.01); *A61B 8/56* (2013.01); *G06Q 10/101* (2013.01); *G06Q 50/22* (2013.01); *G16H 30/20* (2018.01); *G16H 40/20* (2018.01); *G16H 40/40* (2018.01); *G16H 40/63* (2018.01)

(58) Field of Classification Search
CPC ........ G16H 40/20; G16H 40/40; G06Q 10/06; G06Q 10/0631
USPC ...................... 705/2–3, 7.12–7.26
See application file for complete search history.

(56) References Cited

U.S. PATENT DOCUMENTS

| | | |
|---|---|---|
| 5,370,120 A | 12/1994 | Oppelt et al. |
| 6,705,995 B1 | 3/2004 | Poland et al. |
| | (Continued) | |

FOREIGN PATENT DOCUMENTS

| | | |
|---|---|---|
| DE | 10 2005 056 081 A1 | 6/2007 |
| EP | 2 799 013 A1 | 11/2014 |

OTHER PUBLICATIONS

Dallessio, Kathleen M. "The future of ultrasound: A conversation with Arnd Kaldowski." Applied Radiology 35.6 (2006): 44. (Year: 2006).*

(Continued)

*Primary Examiner* — Mark Holcomb (57) ABSTRACT

A method executed at least in part by a computer and comprising responding to an instruction requesting an ultrasound exam by wirelessly communicating with an ultrasound system by transmitting a query signal and receiving a response signal from the ultrasound system. Response can determine whether or not the ultrasound system is configured with at least a suitable transducer for the requested ultrasound exam. The method determines whether or not an operator identified in the response signal is trained to administer the requested ultrasound exam. A schedule signal for the requested ultrasound exam is transmitted. A displayed message indicates progress of the requested ultrasound exam.

5 Claims, 9 Drawing Sheets

(56) References Cited

U.S. PATENT DOCUMENTS

| | | | |
|---|---|---|---|
| 7,756,724 B2* | 7/2010 | Gropper | G06Q 50/24 |
| | | | 705/2 |
| 7,925,603 B1 | 4/2011 | Laidig et al. | |
| 8,706,516 B2* | 4/2014 | Warner | G06Q 10/10 |
| | | | 705/2 |
| 2003/0069648 A1 | 4/2003 | Douglas et al. | |
| 2006/0004606 A1* | 1/2006 | Wendl | G06Q 10/0631 |
| | | | 705/2 |
| 2006/0143044 A1* | 6/2006 | Conry | G16H 40/20 |
| | | | 705/2 |
| 2007/0288285 A1 | 12/2007 | Nilsson | |
| 2008/0183069 A1 | 7/2008 | Fujimoto | |
| 2009/0132277 A1* | 5/2009 | Molyneaux | G06Q 10/0637 |
| | | | 705/2 |
| 2011/0148624 A1* | 6/2011 | Eaton | G16H 40/63 |
| | | | 340/539.13 |
| 2012/0065987 A1 | 3/2012 | Farooq et al. | |
| 2013/0096444 A1 | 4/2013 | Condurso et al. | |
| 2015/0039336 A1* | 2/2015 | Mayer | A61B 5/0059 |
| | | | 705/2 |
| 2016/0000398 A1 | 1/2016 | Raju et al. | |

OTHER PUBLICATIONS

International Search Report, International application No. PCT/US2017/031866, dated May 10, 2017, 2 pages.

\* cited by examiner

ULTRASOUND SYSTEM AND METHOD

CROSS REFERENCE TO RELATED APPLICATIONS

The present application claims the benefit of U.S. Provisional application U.S. Ser. No. 62/355,369, provisionally filed on 28 Jun. 2016 entitled "ULTRASOUND SYSTEM AND METHOD", in the name of Ajay Anand, incorporated herein in its entirety.

FIELD OF THE INVENTION

The invention relates generally to medical ultrasound systems and methods, and in particular to a method for improved workflow for ultrasound apparatus operation.

BACKGROUND

Ultrasound imaging systems/methods are known, such as those described, for example, in U.S. Pat. No. 6,705,995 (Poland), U.S. Pat. No. 5,370,120 (Oppelt), incorporated herein in their entirety.

Ultrasound utilizes sound waves at frequencies higher than those perceptible to the human ear. Ultrasonic images known as sonograms are generated as a result of pulsed ultrasonic energy that has been directed into tissue using a probe. The probe obtains echoed sound energy from the internal tissue and provides signal content that represents the different sound reflectivity exhibited by different tissue types. This signal content is then used to form images that visualize features of the internal tissue. Medical ultrasound, also known as diagnostic sonography or ultrasonography, is widely used as a diagnostic imaging technique used to help visualize features and operation of tendons, muscles, joints, vessels and internal organs of a patient.

Figure 1:
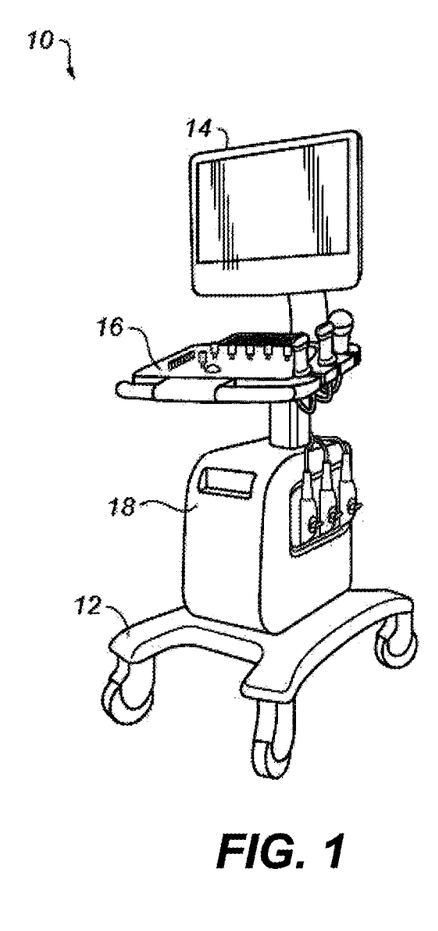
FIG. 1 shows an exemplary ultrasound system.
Figure 2:
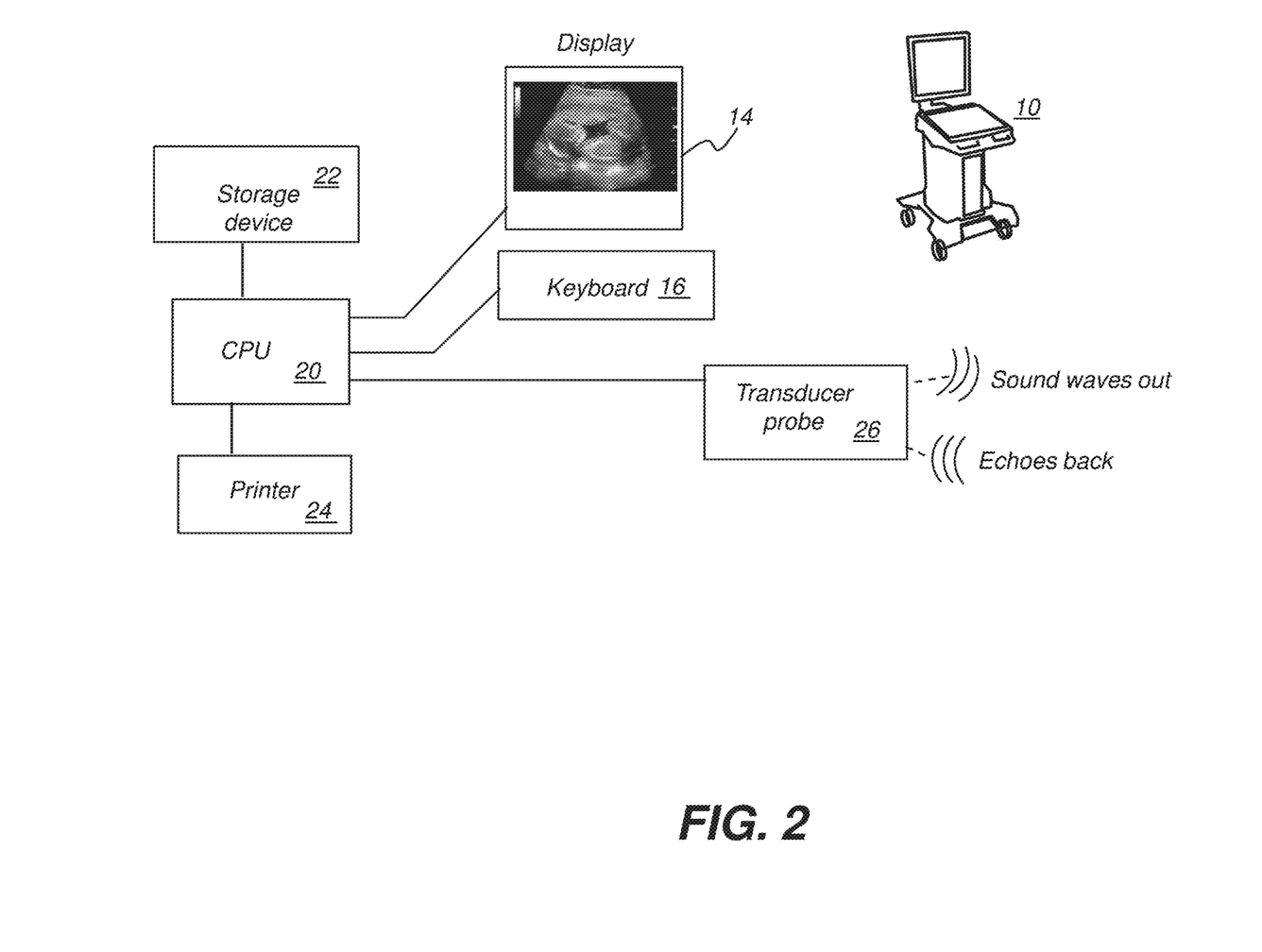
FIG. 2 shows a schematic of an exemplary ultrasound system.

FIG. 1 shows an exemplary portable ultrasound system 10 that uses a cart/base/support, cart 12, a display/monitor 14, one or more input interface devices 16 (such as keyboard or mouse), and a generator 18. The display/monitor 14 can also be a touchscreen to function as an input device. As illustrated, the ultrasound system 10 can be a mobile or portable system designed to be wheeled from one location to another. As FIG. 2 shows, the ultrasound system 10 has a central processing unit CPU 20 that provides control signals and processing capabilities. CPU 20 is in signal communication with display 14 and interface device 16, as well as with a storage device 22 and an optional printer 24. A transducer probe 26 provides the ultrasound acoustic signal and generates an electronic feedback signal indicative of tissue characteristics according to the echoed sound.

Figure 3:
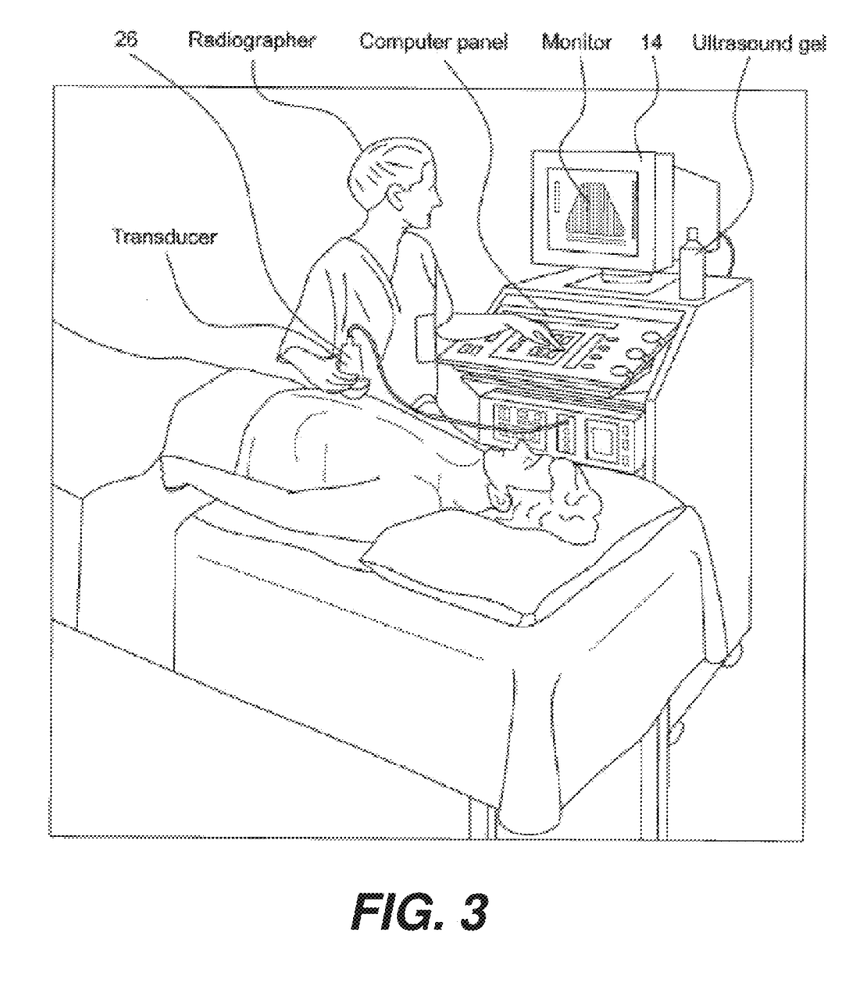
FIG. 3 illustrates a sonographer using an exemplary ultrasound system.

FIG. 3 shows an example of an ultrasound system 10 in use with an image provided on display/monitor 14.

Different types of images, with different appearance, can be formed using sonographic apparatus. The familiar monochrome B-mode image displays the acoustic impedance of a two-dimensional cross-section of tissue. Other types of image can use color or other types of highlighting to display specialized information such as blood flow, motion of tissue over time, the location of blood and other fluid, the presence of specific molecules, tissue stiffness, or the anatomy of a three-dimensional region.

Accordingly, the ultrasound systems of FIGS. 1-3 are typically configured to operate within at least two different ultrasound modes. High-end systems can have capabilities not available in more portable, less fully featured equipment. Continuing improvements in electronics packaging and miniaturization, component manufacture, processing technology, and ergonomic design have contributed to making ultrasound equipment more accessible and more readily usable, allowing the development of increasingly portable systems, including systems of laptop scale for bedside use. At the same time, specialized capabilities that may be used less frequently or require high operator skill may be available on some types of equipment but not other less complex systems. A particular hospital or other care facility may have a number of different ultrasound systems of varying capabilities, with particular systems primarily allocated to different functions.

Ultrasound imaging systems can be employed in mobile and ambulatory environments such as the emergency room, outpatient clinics and non-radiology settings. The environment in these settings can be fluid and dynamic, as compared to a traditional radiology clinic where procedures are planned, appointments are scheduled, and the workflow is pre-determined.

In a traditional radiology setting, depending on the clinical indications for a given ultrasound exam, a suitable ultrasound machine for a given imaging type is pre-selected (depending on its features) so that the clinical output from the exam is optimal and leads to correct follow-up for the patient. Planning and scheduling within the radiology department allocate equipment and staff resources to manage the ongoing workload. In contrast, in an ambulatory environment or emergency room setting, advance planning is necessarily limited. Decisions are typically made on the spot; accordingly, for a given patient condition an ultrasound system may need to be procured immediately or with short notice. Equipment allocation can vary from one hour or work shift to the next and it can be difficult for the medical team to determine what type of ultrasound system is currently available and would work best for handling a particular situation.

The use of portable ultrasound equipment for various types of testing allows improved distribution of this equipment within a medical facility and makes it possible to quickly deploy a system at a patient's bedside or other location not typically used for ultrasound imaging. However, resource allocation can present more complex problems, since systems can be configured differently and operators may not be as readily available or able to respond as desired in each case.

Thus, there exists a need for a method for allocating ultrasound resources more effectively, particularly in mobile and ambulatory environments.

SUMMARY

According to one aspect of the invention, there is provided a system and method for automated ultrasound system identification, for locating ultrasound equipment within a facility, and for improved allocation of ultrasound resources. An object of the present disclosure is to advance the art of ultrasound imaging and to provide a method and apparatus that can help to automate and expedite the delivery of ultrasound imaging services within a health care facility.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present disclosure, there is provided a method executed at least in part by a computer and comprising: responding to an instruction requesting an ultrasound exam by: (i) wirelessly communicating with an ultrasound system by transmitting a query signal and receiving a response signal from the ultrasound system; (ii) determining from the response signal whether or not the ultrasound system is configured with at least a suitable transducer for the requested ultrasound exam; (iii) determining whether or not an operator identified in the response signal is trained to administer the requested ultrasound exam; transmitting a schedule signal for the requested ultrasound exam to the ultrasound system; and displaying a message indicating progress of the requested ultrasound exam.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF EXEMPLARY EMBODIMENTS

The following is a detailed description of the embodiments of the invention, reference being made to the drawings in which the same reference numerals identify the same elements of structure in each of the several figures.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless, such as using a local WiFi network. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" or "body" or "anatomy" is used to describe a portion of the patient that is undergoing ultrasound imaging. The terms "sonographer", "technician", "viewer", "operator", and "practitioner" are used to indicate the person who actively operates the sonography equipment.

The term "highlighting" for a displayed element or feature has its conventional meaning as is understood to those skilled in the information and image display arts. In general, highlighting uses some form of localized display enhancement to attract the attention of the viewer. Highlighting a portion of a display, such as a particular value, graph, message, or other element can be achieved in any of a number of ways, including, but not limited to, annotating, displaying a nearby or overlaying symbol, outlining or tracing, display in a different color or at a markedly different intensity or grayscale value than other image or information content, blinking or animation of a portion of a display, or display at larger scale, higher sharpness, or contrast.

The ultrasound system, shown by way of example in FIG. 1, can include image processing system, a user interface and a display. The image processing system includes a memory and a processor. Additional, different or fewer components may be provided in the system or image processing system. In one embodiment, the system is a medical diagnostic ultrasound imaging system. The memory is a RAM, ROM, hard drive, removable media, compact disc, DVD, floppy disc, tape, cache memory, buffer, capacitor, combinations thereof or any other now known or later developed analog or digital device for storing information. The memory is operable to store data identifying a selected point for identifying a region of interest. The memory is operable to store data identifying one or a plurality of region of interest.

Information from the user interface indicating a position on an image on the display is used to determine a spatial relationship of a user-selected point to a scanned region or to an image position. The selected point is an individual or single point in one embodiment that may be a point selected within a line, area, or volume. Additional or different information may be also stored within the memory. The processor can be a general processor, application-specific integrated circuit, digital signal processor, controller, field programmable gate array, digital device, analog device, circuit formed using an arrangement of transistors or combinations thereof, or other now known or later-developed devices for receiving analog or digital data and outputting altered or calculated data signal content.

The user input device for an ultrasound apparatus can be a track ball, mouse, joy stick, touch pad, buttons, slider, knobs, position sensor, combinations thereof or other now known or later-developed input devices. The user input is operable to receive coordinates of a selected point from a user. For example, the user positions a cursor on an image that appears on the display. The user then selects a position of the cursor as indicating a point for a region of interest.

The display for an ultrasound system can be a CRT, LCD, plasma screen, projector, combinations thereof, or other now known or later-developed device for displaying an image, a region of interest, region of interest information and/or user input information.

Modes of ultrasound used in medical imaging include the following:
  A-mode: A-mode (amplitude mode) is the simplest type of ultrasound. A single transducer scans a line through the body with the echoes plotted on screen as a function of depth. Therapeutic ultrasound aimed at a specific tumor or calculus also uses A-mode emission to allow for pinpoint accuracy in focus of the destructive wave energy.

B-mode or 2D mode: In B-mode (brightness mode) ultrasound, a linear array of transducers simultaneously scans a plane through the body that can be viewed as a two-dimensional image on screen. Sometimes referred to as 2D mode, B-mode operation is generally the starting point for exam types that use other modes.

C-mode: A C-mode image is formed in a plane normal to a B-mode image. A gate that selects data from a specific depth from an A-mode line is used; the transducer is moved in the 2D plane to sample the entire region at this fixed depth. By way of example, when the transducer traverses the area in a spiral, an area of 100 $cm^2$ can be scanned in around 10 seconds.

M-mode: In M-mode (motion mode) ultrasound, pulses are emitted in quick succession. With each pulse, either an A-mode or B-mode image is acquired. Over time, M-mode imaging is analogous to recording a video in ultrasound. As the organ boundaries that produce reflections move relative to the probe, this mode can be used to determine the velocity of specific organ structures.

Doppler mode: This mode makes use of the Doppler effect in measuring and visualizing blood flow.

Color Doppler: Velocity information is presented as a color-coded overlay on top of a B-mode image. This mode is sometimes referred to as Color Flow or color mode.

Continuous Doppler: Doppler information is sampled along a line through the body, and all velocities detected at each point in time are presented (on a time line).

Pulsed wave (PW) Doppler: Doppler information is sampled from only a small sample volume (defined in 2D image), and presented on a timeline.

Duplex: a common name for the simultaneous presentation of 2D and (usually) PW Doppler information. (Using modern ultrasound machines, color Doppler is very widely used; hence the alternative name Triplex).

Pulse inversion mode: In this mode, two successive pulses with opposite sign are emitted and then subtracted from each other. This implies that any linearly responding constituent tends to disappear while gases with non-linear compressibility are accentuated. Pulse inversion may also be used in a similar manner as in Harmonic mode.

Harmonic mode: In this mode a deep-penetrating fundamental frequency is emitted into the body and a harmonic overtone is detected. With this method, noise and artifacts due to reverberation and aberration are greatly reduced. Some practitioners hold that penetration depth can be gained with improved lateral resolution; however, this is not well documented.

Elastography mode: this mode maps the elastic properties of soft tissue. Tissue response indicating hardness or softness can yield diagnostic information about the presence or status of disease. For example, cancerous tumors are often noticeably harder than the surrounding tissue, and diseased livers stiffer than healthy ones.

In order to better understand factors that can affect ultrasound system resource allocation, as addressed by methods and apparatus of the present disclosure, it is useful to categorize these ultrasound imaging modes as either of the following:

(i) survey modes. This category includes more static ultrasound modes that broadly enable the patient anatomy that is under study to be identified and includes A-mode, B-mode, C-mode, M-mode, and harmonic mode. The survey modes can be considered as mapping modes, using acoustic energy to identify and present the overall anatomy of interest as the overall region of interest (ROI). Survey mode scanning is characterized by relatively low energy levels and moderate to low computational demands with relatively straightforward computation. Survey mode scanning tends to generate broader areas of image content, so that the image coverage is sufficient to include the region of interest and surrounding portions of the anatomy. In conventional practice, initial measurements of the patient are obtained in a survey mode and the ROI is displayed accordingly. In medical applications, there are no significant anatomy-related constraints for imaging type for typical survey modes. B-mode imaging is the predominant survey mode used in standard practice.

(ii) functional modes: This category includes more specialized, dynamic imaging modes that characterize changing aspects or features of the subject tissue, including temporal attributes such as fluid or gas flow and flow velocity. Other attributes measured using functional mode imaging can include tissue stiffness or elasticity, for example. Functional modes provided with the typical ultrasound system can include shear wave imaging SWEI as well as various types of Doppler imaging, including color Doppler, continuous Doppler, pulsed wave Doppler, and pulse inversion. Functional modes may not be useful over the full ROI defined by the corresponding survey modes and can be limited according to anatomical characteristics.

It should be noted that the identified survey mode and functional mode categories can be used in any sequence that provides useful results; however, the general workflows for imaging typically begin with a survey mode to help orient the practitioner or sonographer to the anatomy being studied, and then follow with one or more functional modes to obtain specialized data. Moreover, survey modes can be repeated in a workflow, such as in situations where it can be useful to obtain further definition of a particular location for subsequent functional mode imaging.

While conducting an ultrasound exam, the sonographer may often switch between multiple ultrasound modes. In conventional practice, for example, the sonographer first operates in a B-mode in order to coarsely locate the ROI. The sonographer then transitions to a Doppler mode before moving back to the B-mode. For some particular examinations, there are pre-set (or pre-determined or pre-defined) steps and a predetermined sequence of modes that the sonographer routinely follows. That is, the ordered sequence of modes used in a particular exam type can be predefined for the operator.

For carotid artery imaging, for example, the exam typically follows a progression of modes such as the following:
(i) B-mode for initial positioning and establishing reference coordinates of the sample volume;
(ii) Color Flow mode for improved visualization of blood vessels; and
(iii) Pulse wave Doppler mode for highlighting blood flow within the sample volume.

For heart imaging, the exam progression can use B-mode or M-mode imaging for auto-positioning of the cursor, followed by Color Flow or pulse wave Doppler modes.

Figure 4:
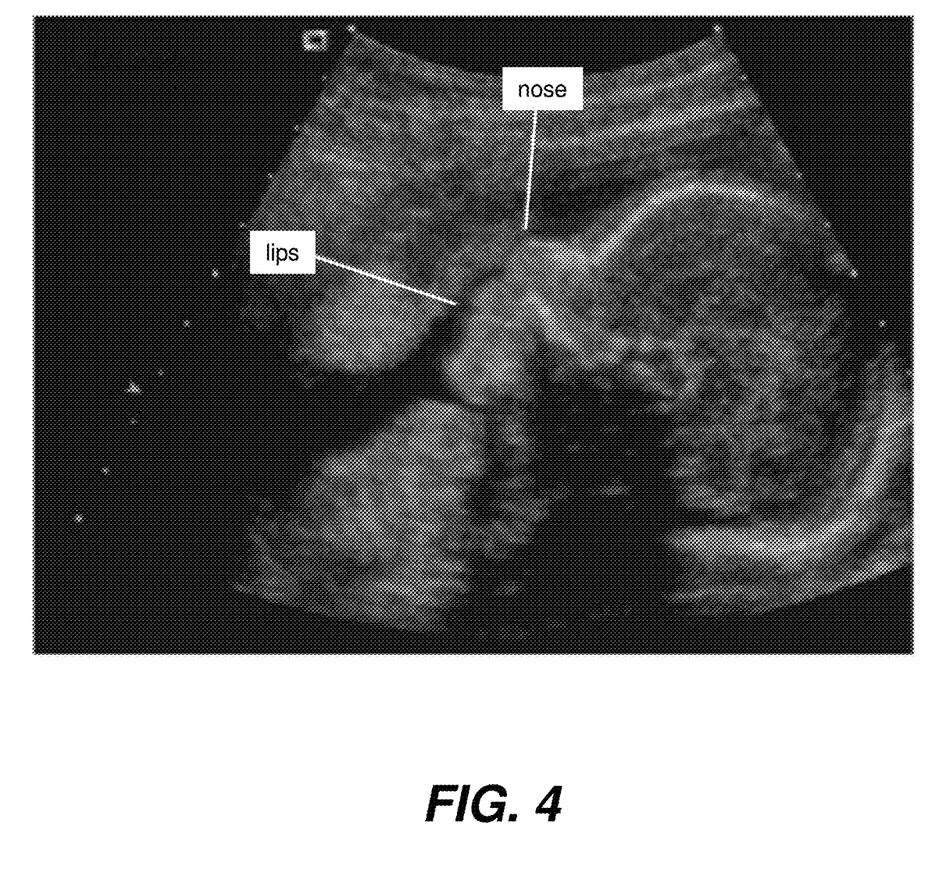
FIG. 4 shows a displayed B-mode ultrasound image.

The sonography workflow typically begins with acquisition and display of a grayscale mode image (such as the B-mode image illustrated in FIG. 4) in order to survey the anatomy. FIG. 4 shows an exemplary B-mode ultrasound image, displayed as a grayscale image. After the B-mode image is acquired, however, sonographer workflow can vary significantly, with selection of more complex imaging modes and settings more suitable for specialized imaging.

Ultrasound resource allocation must consider both equipment capabilities and staff expertise. With respect to equipment, some common functions are available with at least the majority of ultrasound systems, such as conventional B-mode imaging. Low-end ultrasound apparatus and earlier equipment, however, may not be configurable to support more specialized imaging modes that require more complex signal generation and processing software or utilize more costly transducer probes. With respect to staffing, more complex and specialized imaging modes can require training and experience that is at a skill level beyond what is normally practiced in routine ultrasound examination.

Figure 5:
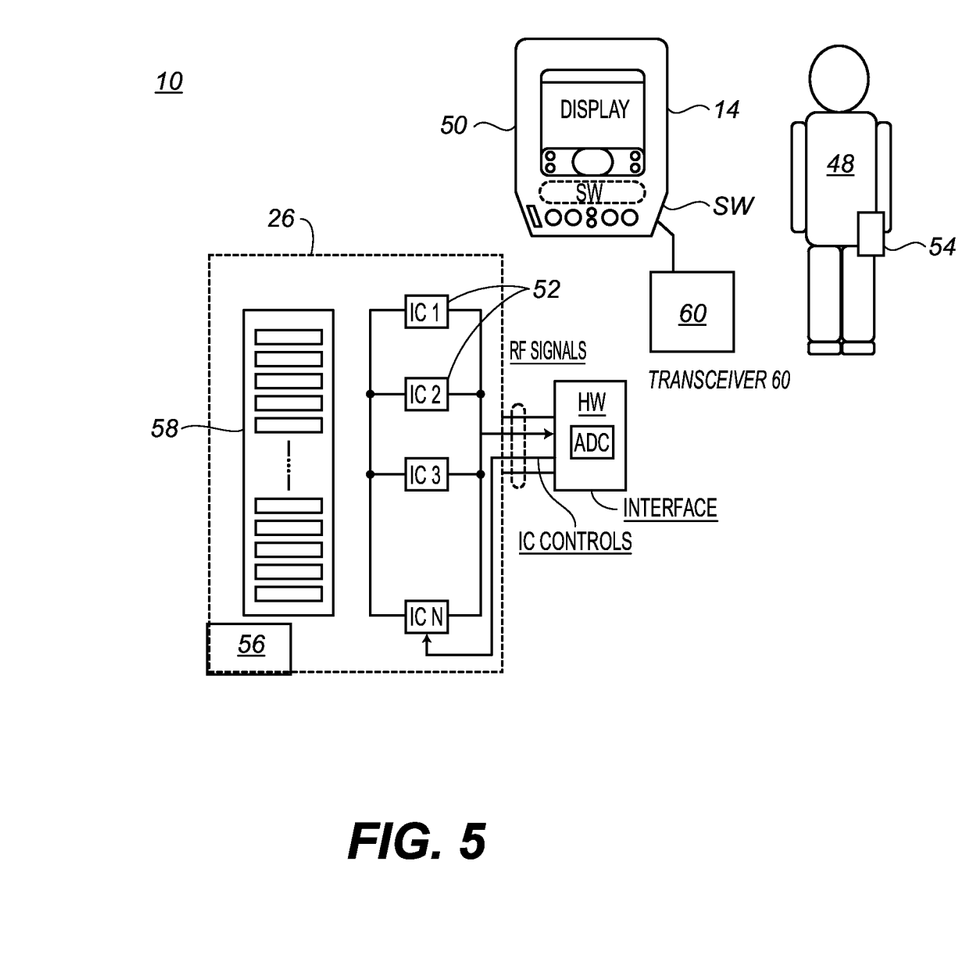
FIG. 5 shows components of an ultrasound system.

The schematic diagram of FIG. 5 shows components of an ultrasound system 10 according to an embodiment of the present disclosure. An array 58 of transducer elements in probe 26 provides signals to operating software SW in a processor 50 for processing and display on display monitor 14. Integrated circuits 52 provide the needed signals for ultrasound generation. Communication with centralized host processor equipment and with operator validation and badging using a key fob, badge, or other identification mechanism can be through a transceiver 60. The sonographer 48 can have a badge 54 that authorizes the sonographer to acquire images and helps to identify and validate a system user.

Ultrasound Resource Tracking

Embodiments of the present disclosure provide a way to improve allocation of ultrasound resources to address the dynamic and changing needs of hospital patients and others in a health-care facility. Ultrasound resources can include both equipment, such as individual ultrasound sensing apparatus, specialized transducer types, and sonographer personnel, who can be identified by badging or other login or authentication mechanisms and whose identification can be linked to personnel, scheduling, billing, and training records accessible to the system, for example.

Figure 6:
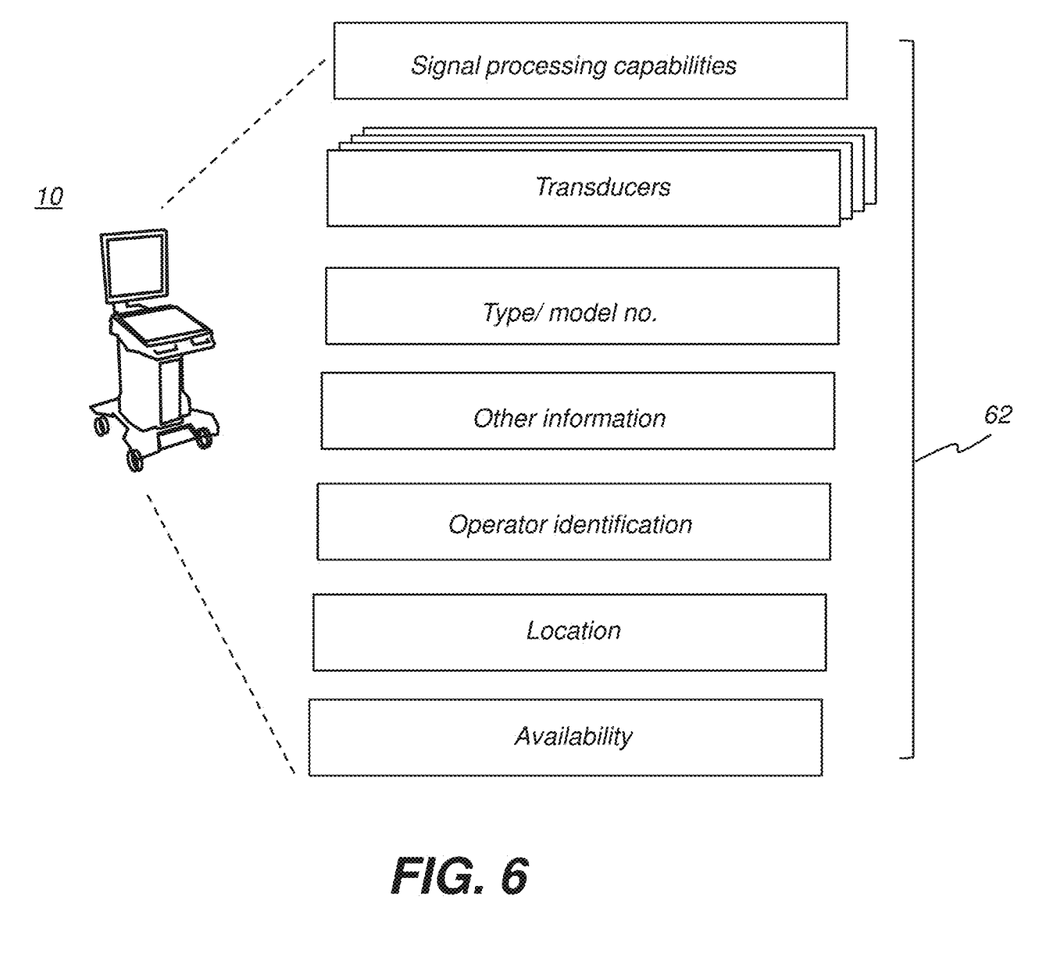
FIG. 6 shows a diagram for data stored about an ultrasound system.

The ultrasound system 10 can have a significant amount of associated data, stored and available when queried by a host processor. The schematic diagram of FIG. 6 shows various exemplary types of data 62 that can be obtained and stored for ultrasound system 10 and can be usable to a system for tracking, allocating, and managing ultrasound resources. Data 62 can include signal processing capabilities for a system, including a listing of modes, available settings, and other data that relate to readiness and suitability for executing specific types of exam.

The ultrasound system 10 can also store data on transducers that are currently available with the system. Transducers can be sector, linear, curvilinear, phased array, or convex types, or other specialized transducer type, such as micro-convex. According to an embodiment of the present disclosure, each transducer 26 has an identifying tag 56 (FIG. 5), such as an RF ID tag, that can be detected by circuitry on the ultrasound or scheduling system, such as by polling. Since transducers 26 can be of general or of specialized types, and because these devices can be stored with the ultrasound system, a straightforward resource tracking solution is simply to identify the location and system ID that relate to each of the available ultrasound probes.

System 10 can also store manufacturer type and model number, as well as other metadata about the ultrasound hardware and software components. This can include calibration data, for example. In addition, stored metadata can include information on quality assurance testing.

The information about ultrasound system 10 can be stored for availability from a central host processor or database. Alternately, one or more parts of this information can be generated and stored directly on the ultrasound system 10 itself, so that up-to-date information about the system 10 can be more readily accessible. A polling arrangement can be used to query an ultrasound system in order to determine its capabilities and suitability for particular exams. Polling can be executed periodically, such as at regular intervals or following a certain number of hours of used, or on an as-needed basis. Operator identification can also be used to determine whether or not a particular operator has appropriate training to run a particular exam type.

As part of resource tracking, ultrasound system 10 can identify each operator that is currently using the system. Operator identification can be performed in a number of ways, such as using a badge reader or by identifying an operator login, for example. Operator identification can then be linked with other data about the operator, such as an operator profile that outlines training, level of experience, exams for which the operator is qualified, schedule demands, workload, and the like. While choosing the optimal system for the patient in a particular instance, consideration could also be given to the operator's experience or preference in working with available systems. Operational or ergonomic attributes of the system such as user interface type (e.g. touch screen or knob-button based), available degree of adjustment (top-down, swivel), connectivity (detachable keyboard) could be included in the decision-making process for choosing the optimal system.

Ultrasound system 10 also stores information or indicators that allow ready detection of its location at a facility. In addition, the state of availability of the ultrasound system for use on an emergency or as-needed basis can be readily determined.

Figure 7:
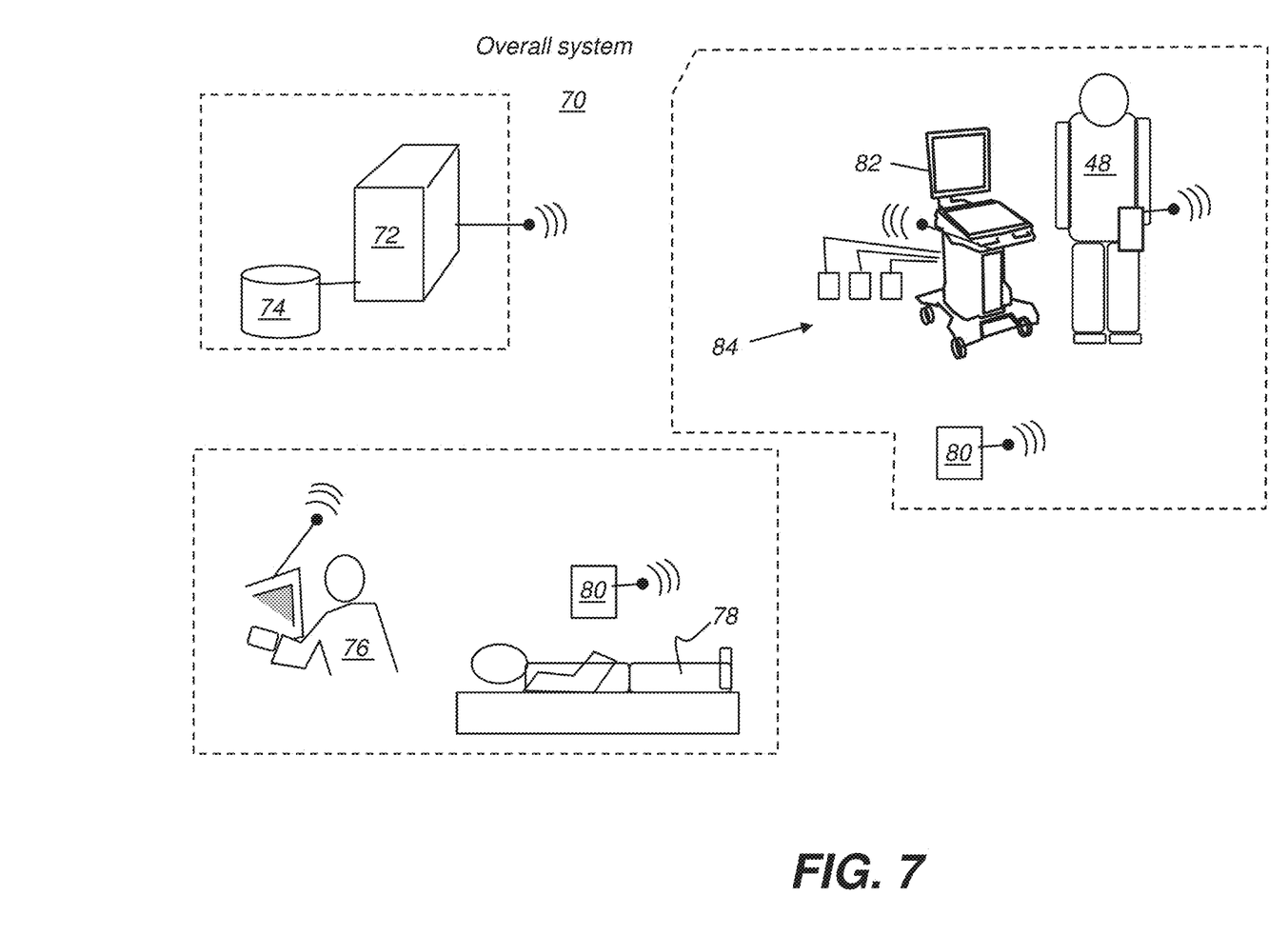
FIG. 7 shows a tracking system that can be suitable for a hospital, clinic, or other setting wherein ultrasound use may be required on an as-needed basis.

The schematic diagram of FIG. 7 shows a tracking system 70 that can be suitable for a hospital, clinic, or other setting wherein ultrasound use may be required on an as-needed basis. Dashed boxes indicate parts of the system that can be at different locations within a facility. A host processor 72 is in signal communication with a memory 74 or database utility that can store useful information about various ultrasound equipment that may be accessed at a site. Wireless data transmission can be used to track equipment and operator locations, such as using routers 80 of an existing Wi-Fi network at the site or using some type of dedicated wireless network.

In an example case, a physician, nurse, or other practitioner 76 treats a patient 78 and determines that an ultrasound image may serve a useful diagnostic function. Practitioner 76 sends a request to host processor 72 that coordinates equipment allocation within system 70. As part of the request, the practitioner 76 indicates a patient condition or symptom that suggests ultrasound use for imaging in a particular mode. A query signal transmits request data to one or more nearby ultrasound systems. A portable ultrasound system 82 is located on the same floor of the facility, equipped with suitable transducers 84 and operating capabilities for handling the indicated symptom or condition. Information provided about the system can include operator training and availability for the needed imaging type.

The capability for identifying the sonographer 48 who is associated with a particular ultrasound system 82 allows conventional paging systems to be used when it is desirable to obtain ultrasound imaging services or assistance.

According to an embodiment of the present disclosure, portable ultrasound system 82 maintains tracking information on transducers 84 that currently reside with the system. Each transducer 84 can have a radio-frequency identification (RFID) tag, a sensor-detectable component, or an optical encoding that is readable by a processor on system 82. The types of connected or available transducers 84 for each system can be provided when system 82 is polled, as described subsequently.

Figure 8:
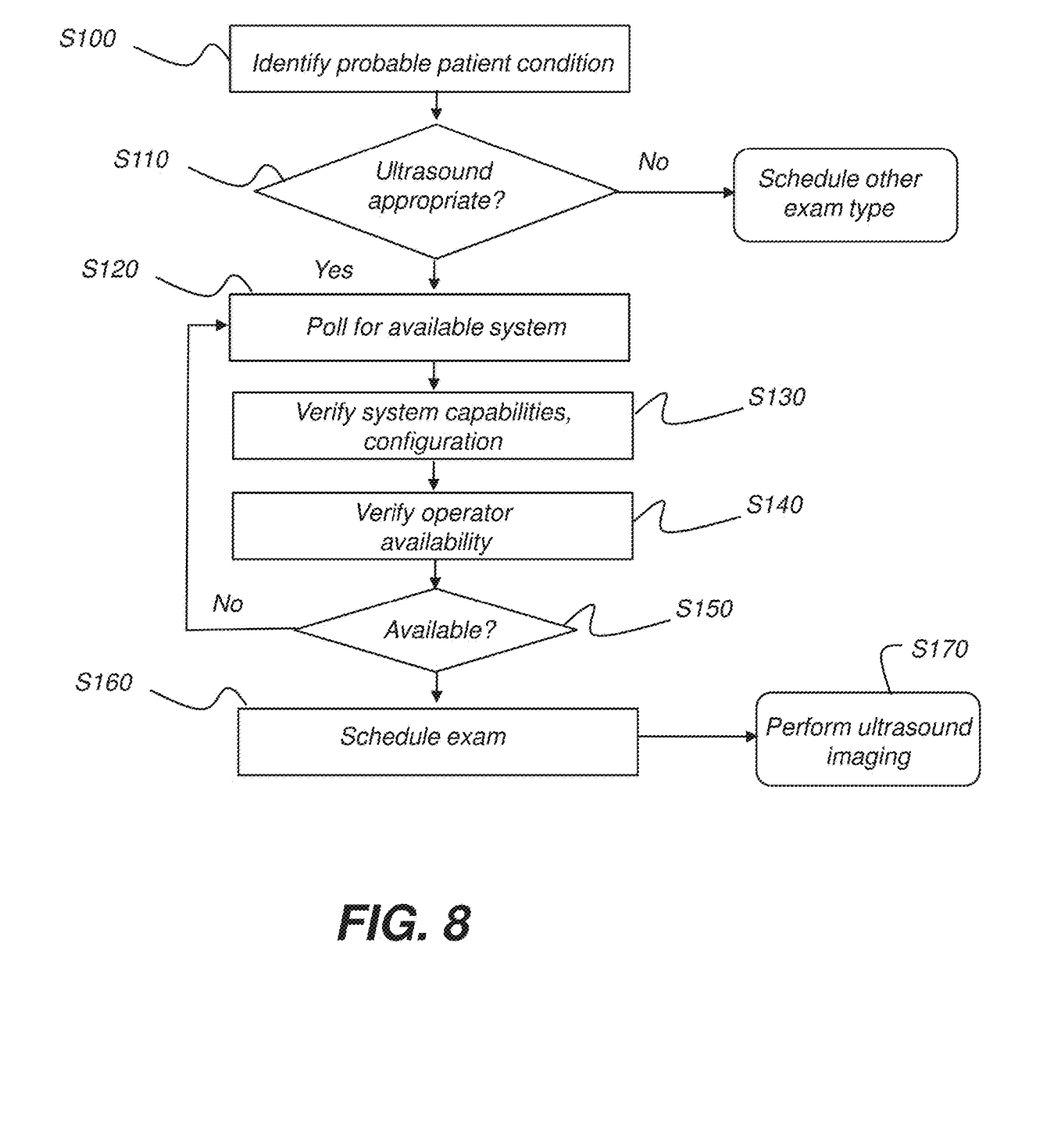
FIG. 8 is a logic flow diagram that shows exemplary processing steps for ultrasound system allocation according to an embodiment of the present disclosure.

The logic flow diagram of FIG. 8 shows exemplary processing steps for ultrasound system allocation according to an embodiment of the present disclosure. These steps are executed in response to practitioner instructions and can be executed by the host processor 72 (FIG. 7) or other computer host. In an identification step S100, the practitioner identifies the patient condition that may benefit from an ultrasound exam. In a decision step S110, system logic determines whether or not ultrasound is appropriate for the identified condition. If not, the host may specify another type of exam or procedure. If ultrasound may be useful, the host processor executes a polling step S120 that determines and indicates what type of ultrasound exam to request and checks for an available system. A system verification step S130 checks the ultrasound system type, capabilities, and configuration to determine whether or not an available system can execute the needed exam. Verification step S130 can test for available signal types, transducer types and condition, and other variables that determine system capability. Different transducers may serve different purposes and some specialized types of transducers may not be standard equipment with particular systems.

Continuing with the flow of FIG. 8, an operator verification step S140 checks to determine whether or not a suitable operator is available. Step S140 can also determine whether or not a particular operator has appropriate training and skill level to perform a needed exam type. For example, an operator may not have sufficient training or experience to perform a cardiac ultrasound exam that may be necessary in the emergency evaluation of a trauma patient. A test step S150 then allows the process to continue where equipment is available and suitable or, if equipment availability, configuration, or operator expertise are insufficient, returns to polling step S120 to check for an alternate system in response to the practitioner request. If the system is suitable and available and the operator can be assigned the imaging task, a scheduling step S160 executes, providing a job order or other assignment to the sonographer or other operator. The job order can display as a message appearing on the ultrasound monitor, for example. A message can also be posted on a personnel paging system in the hospital or other facility. Scheduling software logic for the facility can also be notified of a change that has been requested, such as on an emergency basis. Step S160 can transmit an alert signal to the operator or paging system, for example. When the job is scheduled, a confirmation message can be displayed. Progress of the job, from request and scheduling to completion, can be provided to the requesting practitioner or other authorized personnel.

Other information that can be available to support the FIG. 8 workflow can include battery level information for the ultrasound equipment and support for add-on devices. Add-on devices that may be requested can include biopsy guides, needle tracking software, and fusion software support, such as for CT (computed tomography) with ultrasound imaging or Magnetic resonance imaging (MRI) with ultrasound diagnostics.

In addition to conventional ultrasound diagnostics, specialized software, such as that described in U.S. Patent Application No. 2016/0000398 entitled "Scanning to Identify and Delimit Stationary Fluid Pools" by Raju et al. can be used to highlight clinical information (e.g. blood pools and air pockets) using unique acoustic signatures on an ultrasound image. For some cases, access to an ultrasound system with such ultrasound diagnostics capability can be particularly useful and require trained personnel.

An execution step S170 then allows ultrasound imaging and display to proceed, according to the specified setup. The system can provide a message indicating exam status, such as scheduling information. Following exam execution, a message indicating exam completion can be sent to the system processor and to appropriate personnel.

Operator Interface

Figure 9:
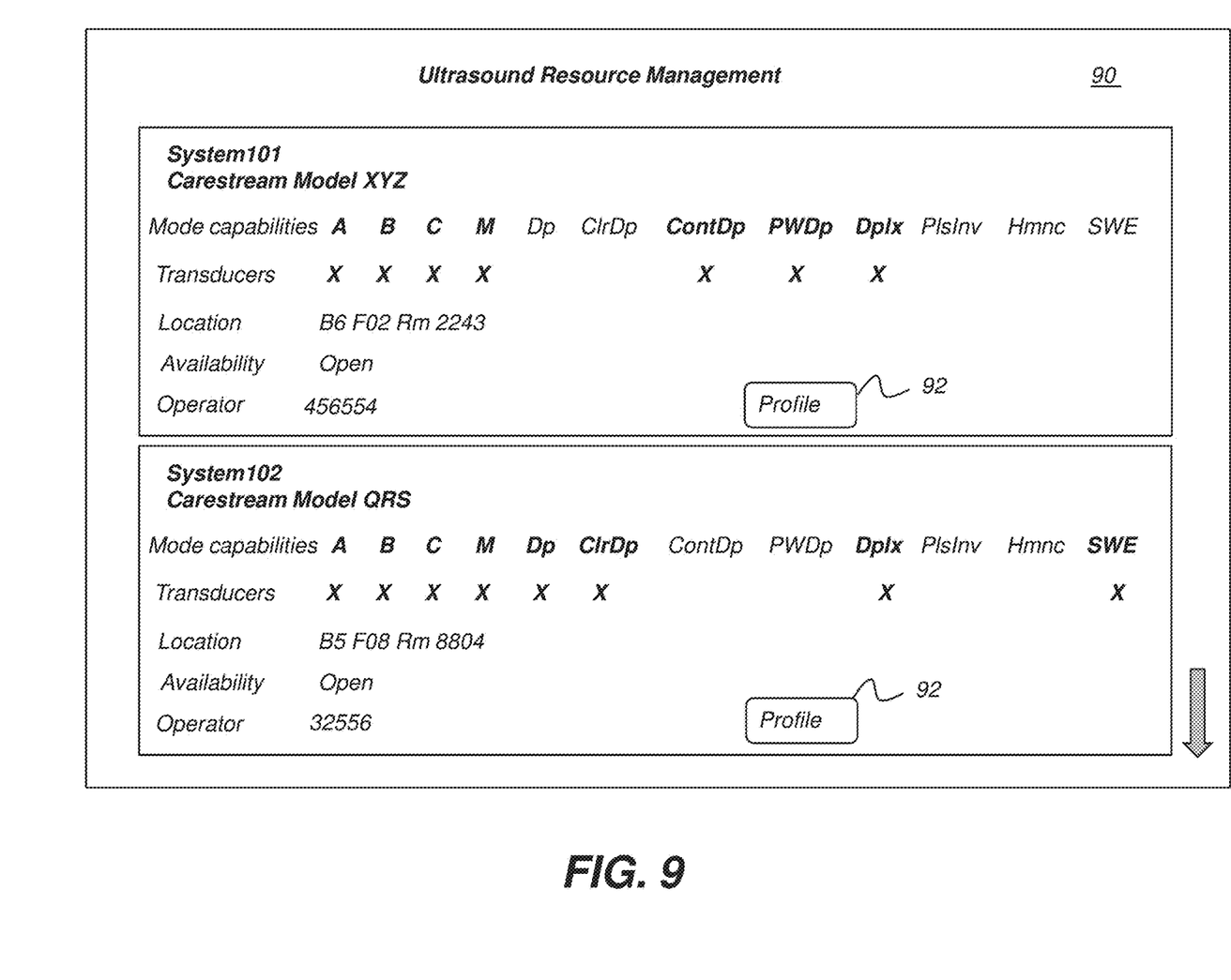
FIG. 9 is an example operator interface for portable ultrasound resource management.

FIG. 9 is an example operator interface for portable ultrasound resource management. Available to the practitioner as part of steps S120, S130, S140, and S150 of the FIG. 8 sequence, an operator interface screen 90 presents identifying and capabilities information about portable ultrasound equipment that may be available for allocation in an emergency or to meet some other clinical requirement. As the example shows, information can be listed by location proximity and availability, as well as by criteria such as suitability to a particular mode or exam type. Automated custom software for specific clinical indications could also be listed on the display, indicating whether a given system could provide a more customized workflow for the type of examination at hand. Available operating modes can be highlighted in bold, for example. Available modes and transducers that are provided with the system can be reported. Operators can be listed, along with operator profile information, such as selectable by a control button 92, that can list training, scheduling availability, and other useful data about the ultrasound operator. On-screen scroll tools can be provided for listing available systems based on selectable criteria.

In the event that a particular transducer is not provided with the system and operator requested, the ultrasound resource management utility can send a message to another system operator, requesting that the transducer be transferred to the desired system or acquired from a storage facility. This feature can help to improve cost efficiency for the ultrasound equipment, so that specialized transducers that are not needed for standard exams do not need to be resident with a particular system, but can be available for requisition on an as-needed basis.

An operator interface can be provided that allows the practitioner to identify the patient condition and that uses programmed logic to match the condition with a particular type of ultrasound exam that can be executed by one or more ultrasound apparatus located at the medical facility or other site. The interface can then display the location of the ultrasound apparatus and provide any other useful information, such as tracking number assigned to the apparatus at the site. The interface can then identify and display information about availability of one or more available operators who are trained to perform the identified exam. It can be appreciated that the programmed logic that is used can employ learning software that takes advantage of historical data at the site in order to select or recommend an exam type according to indicated patient symptoms or condition. Where particular ultrasound exams may be recommended, the tracking utility can also identify and report which system or systems are suitably equipped for the exam, such as by identifying and tracking transducer types stored with each system. The interface software utility can also provide a mechanism for alerting the sonographer or other operator personnel, including directing a signal to the operator or providing a message on a paging system.

EXAMPLE

The attending physician requests an urgent ultrasound exam for evaluating abdominal trauma using the FAST (Focused Assessment with Sonography in Trauma) or eFAST exam. The FAST ultrasound examination is a useful procedure for the evaluation of the torso for bleeding after traumatic injury, particularly blunt trauma, but it may also be helpful in penetrating injury. This specialized exam type often requires a specially trained sonographer and an ultrasound system that offers customized protocols. Systems with enhanced reporting, workflow enhancement and measurement capabilities can be particularly valuable for FAST exam use.

A request instruction is transmitted from patient bedside to the host processor, specifying ultrasound resource allocation. Host processor 70 (FIG. 7) checks it's tracking database in memory 74 to determine which resources are available for the required exam function. If an available system is located, the request is directed to a log or assignment function for the system and corresponding sonographer and entered into a job listing or other assignment mechanism for exam execution.

An embodiment of the present disclosure can be implemented as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

In the following claims, the terms "first," "second," and "third," and the like, are used merely as labels, and are not intended to impose numerical or ordinal requirements on their objects, such as necessarily requiring a specific operational sequence.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method, executed at least in part by a computer, comprising:
    responding to an instruction requesting an ultrasound exam by:
        polling a plurality of ultrasound systems by transmitting a query signal and receiving a response signal from each of the plurality of ultrasound systems, wherein the response signals each identify:
            a transducer type of the responding ultrasound system, wherein a radio-frequency identification ("RFID") signal is used to determine the transducer type of the responding ultrasound system, and
            an operator associated with the responding ultrasound system and a capability of the responding ultrasound system;
        determining from the received plurality of response signals that one or more of the responding ultrasound systems is sufficiently configured with:
            a suitable transducer type for performing the requested ultrasound exam and the capability to perform the requested ultrasound exam;
        determining from the received plurality of response signals that one or more of the responding ultrasound systems is insufficiently configured by not having a suitable transducer type for performing the requested ultrasound exam or by not having the capability to perform the requested ultrasound exam;
        determining whether or not the operator identified in the response signal is sufficiently trained to administer the requested ultrasound exam using the responding ultrasound system that is sufficiently configured and associated with the operator identified in the response signal;
        in response to determining that the operator identified in the response signal is sufficiently trained to administer the requested ultrasound exam using the associated sufficiently configured ultrasound system and in response to determining that the responding ultrasound system is available,
            transmitting a schedule signal for the requested ultrasound exam to the associated sufficiently configured ultrasound system; and
            displaying a message indicating progress of the requested ultrasound exam.

2. The method of claim 1, wherein transmitting the schedule signal comprises paging the sufficiently trained operator.

3. The method of claim 2 further comprising adjusting a schedule associated with the sufficiently trained operator and the associated sufficiently configured ultrasound system.

4. The method of claim 1, further comprising using an RFID signal to determine a transducer type of the responding ultrasound system.

5. The method of claim 1, further comprising accessing an operator profile to determine whether or not the operator identified in the response signal is sufficiently trained to administer the requested ultrasound exam.

\* \* \* \* \*